United States Patent
Beuzard et al.

(10) Patent No.: US 6,464,998 B1
(45) Date of Patent: *Oct. 15, 2002

(54) COMPOSITION FOR THE IN VIVO PRODUCTION OF THERAPEUTIC PRODUCTS

(75) Inventors: Yves Beuzard, Paris; Olivier Danos, Garches; Vincent Descamps, Marly le Roi; Jean-Michel Heard, Paris; Philippe Moullier, Meudon; Nadia Naffakh, Malakoff; Michel Perricaudet, Ecrosnes; William Vainchenker, Paris, all of (FR)

(73) Assignee: Aventis Pharma S.A., Antony (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/649,696

(22) PCT Filed: Nov. 22, 1994

(86) PCT No.: PCT/FR94/01359

§ 371 (c)(1),
(2), (4) Date: Jul. 11, 1996

(87) PCT Pub. No.: WO95/14785

PCT Pub. Date: Jun. 1, 1995

(30) Foreign Application Priority Data

Nov. 23, 1993 (FR) .............................................. 93 13977

(51) Int. Cl.$^7$ ............................ A61F 13/00; C12N 5/02; C12N 15/63; C07H 21/04
(52) U.S. Cl. ........................ 424/422; 435/325; 435/382; 435/395; 435/397; 435/400; 435/455; 435/456; 435/320.1; 536/23.1; 536/23.2; 536/23.5
(58) Field of Search .......................... 514/44; 424/93.21, 424/424; 435/320.1, 375, 172.3, 325, 382, 395, 397, 400, 455, 456; 536/23.1, 23.5, 23.2

(56) References Cited

U.S. PATENT DOCUMENTS 5,670,488 A * 9/1997 Gregory et al. ................ 514/44

FOREIGN PATENT DOCUMENTS

WO         8907944      * 9/1989
WO      WO 93/06223      4/1993

OTHER PUBLICATIONS

Eck et. al.; Gene-Based Therapy, 1996, In Goodman & Gilman's The Pharmacological Basis of Therapeutics, pp. 77–101.*

Dang et. al.; Gene Therapy and Translational Cancer Research, 1999, Clinical Cancer Research vol. 5: 471–474.*

Marshall; Gerne Therapy'Growing Pains, 1995, Science vol. 269: 1050–1055.*

Riddell et. al.; T–Cell mediated rejection of gene–modified HIV–specific cytotoxic T lymphocytes in HIV–infected patients, 1996, Nature Medicine vol. 2, No. 2: 216–223.*

Hoeben et. al.; Toward Gene Therapy for Hemophilia A: Long–Term Persistence of Factor VIII–Secreting Fibroblasts after Transplantation into Immunodeficient Mice, 1993, Human Gene Therapy 4: 179–186.*

Ridoux et al. NeuroReport 5:801–804, 1994.*

Stratford–Perricaudet et al. J. Clin. Invest. 90:626–630, 1992.*

B Quantin et al Proc Natl Acad Sci 89:2581–2584, 1992.*

C. M. Lynch, et al.; "Long–term Expression Of Human Adenosine Deaminase In Vascular Smooth Muscle Cells Of Rats: A Model For Gene Therapy"; Proc. Natl. Acad. Sci. USA, vol. 89, No. 3, pp. 1138–1142; Feb., 1992.

J. M. Schumacher, et al.; "Intracerebral Implantation Of Nerve Growth Factor–Producing Fibroblasts Protects Striatum Against Neurotoxic Levels Of Excitatory Amino Acids"; Neuroscience vol. 45, No. 3, pp. 561–570; 1991.

S. Yao, et al.; "Expression Of Human Factor IX In Rat Capillary Endothelial Cells: Toward Somatic Gene Therapy For Hemophilia B"; Proc. Natl. Acad. Sci. USA, vol. 88, No. 18, pp. 8101–8105; Sep., 1991.

J. Dhawan, et al.; "Systemic Delivery Of Human Growth Hormone By Injection Of Genetically Engineered Myoblasts"; Science, vol. 254, pp. 1509–1512; Dec., 1991.

W. S. Gallichan, et al.; "Mucosal Immunity And Protection After Intranasal Immunization With Recombinant Adenovirus Expressing Herpes Simplex Virus Glycoprotein B"; Journal of Infectious Diseases, vol. 168, No. 3, pp. 622–629; Sep., 1993.

Corrections and Retraction, *Proc. Natl. Sci. USA*, vol. 89 (1992), p. 7849.

E. J. Kremer et al., "Adenovirus and adeno–associated virus mediated gene transfer," *British Medical Bulletin*, vol. 51, No. 1, (1995), pp. 31–44.

E. J. Kremer et al., "Adenovirus vector–transduced hepatocytes implanted via a preformed collagen/PTFE support persist for at least 4 weeks in vivo," *Gene Ther.*, vol. 3, (1996), pp. 932–936.

(List continued on next page.)

Primary Examiner—Dave T. Nguyen
Assistant Examiner—Quang Nguyen
(74) Attorney, Agent, or Firm—Finnegan, Henderson, Farabow, Garrett & Dunner LLP

(57) ABSTRACT

The present invention provides cell compositions for in vivo implantation, and designed for the sustained and controlled delivery of therapeutic substances.

25 Claims, 1 Drawing Sheet

OTHER PUBLICATIONS

John A. Thompson et al., "Heparin–binding growth factor 1 induces the formation of organoid neovascular structures in vivo," *Proc. Natl. Acad. Sci, USA*, vol. 86, Oct. 1989, pp. 7928–7932.

Palmer et al (1991) Proc. Natl. Acad. Sci. USA 88: 1330–1334.*

Stratford–Perricaudet et al. (1991) Human Gene Transfer 219: 51–61.*

Rosenberg et al (1988) Science 242: 1575–1578.*

Tomita et al (1989) Gene 76: 11–18.*

Watson et al (1987) Mol. Biol. of the Gene, 4th Edition vol. 1, p. 313.*

Medicine/Sciences 9(2):208–10, 1993, Danos Moullier Heard, Reimplantation de cellules genetiquement modifees dans des neo–organes vascularises.

Human Gene Transfer 219:51–61, 1991, Stratford–Perricaudet Perricaudet, Gene transfer into animals: the promise of adenovirus.

* cited by examiner

COMPOSITION FOR THE IN VIVO PRODUCTION OF THERAPEUTIC PRODUCTS

This application is a 371 of PCT/FR94/01359 filed Nov. 22, 1994—immediately below the title of the invention.

The present invention relates to the field of gene and cell therapy. More especially, it relates to cell compositions intended to be implanted in vivo for delivering therapeutic substances in a sustained and controlled manner.

Gene therapy consists in correcting a deficiency or an abnormality (mutation, aberrant expression, and the like) by introducing genetic information into the body of an affected individual. This genetic information may be introduced either in vitro into a cell extracted from the body, the modified cell then being reintroduced into the body, or directly in vivo into the appropriate tissue. Different techniques have been described for introducing this genetic information, including various techniques of transfection involving complexes of DNA and DEAE-dextran [Pagano et al., J. Virol. 1 (1967) 891], of DNA and nuclear proteins [Kaneda et al., Science 243 (1989) 375], and of DNA and lipids [Feigner et al., PNAS 84 (1987) 7413], the use of liposomes [Fraley et al., J. Biol. Chem. 255 (1980) 1043], and the like. More recently, the use of viruses as vectors for gene transfer has been seen to be a promising alternative to these physical transfection techniques. In this connection, different viruses have been tested for their capacity to infect certain cell populations. This applies especially to retroviruses (RSV, HMS, MMS, and the like), the HSV virus, adeno-associated viruses and adenoviruses.

Techniques involving direct administration of the gene in vivo have certain drawbacks, such as the non-selective dispersal of the gene throughout the body, its short half-life, the risks of immunological reaction or alternatively the lack of control of the gene after injection. For this reason, cell therapy offers an advantageous alternative, consisting in removing cells, modifying them ex vivo and then readministering them. As a result, only an identified cell population is modified by the therapeutic gene. However, after administration, the fate of the modified cells is not controlled. Similarly, it is no longer possible to stop the treatment. Lastly, this therapy implies that the cells to be treated can be removed from the body, manipulated ex vivo and readily reimplanted. As a result, it is limited in practice to blood cells.

The present invention provides an advantageous solution to these problems. The present invention relates, in effect, to compositions intended to be implanted in a body, comprising cells modified by a recombinant adenovirus comprising a heterologous DNA sequence coding for a therapeutic product, a gelling agent and a support to which the said cells are anchored.

The implantation of the compositions according to the invention affords many advantages compared to the prior art, and especially control of the number of cells implanted, control of the number of cells infected, measurement of the level of expression of the therapeutic gene before implantation, absence of immunological reaction associated with the direct injection of a virus, possibility of removing the implant at any time, and the like.

The implantation of genetically modified cells has already been envisaged in the prior art. Thus, Palmer et al. [PNAS 88 (1991) 1330] and Moullier et al. [Nature genetics 4 (1993) 154] have described the implantation of fibroblasts genetically modified by retroviruses. However, the use of retroviruses creates some problems limiting the applications of this technology. In particular, retroviruses are difficult to produce at high titres and, as a result, do not permit use at high multiplicities of infection. Retroviruses also have the drawback of not being able to incorporate large-sized fragments of heterologous DNA, thereby limiting the therapeutic applications. Lastly, retroviruses integrate into the genome of fibroblasts, which can contribute to the appearance of tumour cells after implantation. Moreover, the fibroblasts described by Palmer et al. are coated only in collagen, and the implants obtained do not have sufficient cohesion. As a result they gradually disintegrate in vivo, leading to an uncontrolled diffusion of the cells out of the implantation site.

The compositions according to the invention enable these drawbacks to be overcome. The present invention is partly the outcome of the demonstration that adenoviruses are capable of producing in vitro a very high-powered infection of cells in culture. Thus, it is possible to infect 100% of fibroblasts in culture. Moreover, it is also possible, by varying the multiplicity of infection, to obtain a large number of copies of adenovirus per cell (up to 100 copies), thereby enabling the therapeutic effect of the implants of the invention to be substantially increased. Furthermore, the adenoviruses of the invention may be produced at high titres, enabling not only primary cell cultures but also secondary cultures, previously cloned and stored, to be infected. The adenoviruses of the invention also have the advantage of not integrating into the genome of the cells they infect. As a result, the implants of the invention are less likely to induce the appearance of tumour cells. Furthermore, if the implanted cells divide, the adenovirus of the infection will be diluted over generations, and the character it confers on the infected cells will not be transmitted to the daughter cells. Lastly, the adenoviral vectors used in the present invention may be modified so as to incorporate very large-sized fragments of heterologous DNA. Thus, contrary to other viral vectors, it is, for example, possible to incorporate a large-sized heterologous gene such as that for factor VIII or for dystrophin. Furthermore, it is possible to incorporate, in addition to the therapeutic gene, a safety gene whose expression would permit, for example, the destruction of the infected cell.

The compositions according to the invention hence have many advantages compared to the systems described in the prior art, endowing them with much greater therapeutic potentials.

The compositions according to the invention may be made from different cell types, and in particular from fibroblasts, endothelial, epithelial or glial cells, hepatocytes, keratinocytes or alternatively myoblasts. Preferably, fibroblasts are used in the context of the invention.

In a preferred embodiment of the invention, autologous cells, that is to say ones removed from the patient in whom they will then be implanted, are used. However, in some cases, it can be advantageous to use allogeneic or xenogeneic cells, leading to a gradual rejection of the implant and thus giving it an effect which is limited in time. In particular, cells of murine origin may be implanted in man without any effect other than gradual rejection.

The cells used in the context of the invention can be primary cultures. In this case, they can be removed by any technique known to a person skilled in the art, and then cultured under conditions permitting their proliferation. As regards fibroblasts more especially, the latter may be readily obtained from biopsies, for example according to the technique described by Ham [Methods Cell. Biol. 21a (1980) 255]. These cells may be used directly for the preparation of the compositions of the invention, or stored, for example by freezing, for the establishment of autologous banks with a view to subsequent use. Preferably, the compositions according to the invention comprise $10^5$ to $10^{10}$ cells. More preferably, they comprise $10^6$ to $10^8$ cells.

The cells in culture are then infected with recombinant adenoviruses to endow them with the desired therapeutic properties. Infection is carried out in vitro according to techniques known to a person skilled in the art. In particular, depending on the cell type used and the number of copies of virus desired per cell, a person skilled in the art can adapt the multiplicity of infection and, where appropriate, the number of infection cycles carried out. It is obvious that these steps must be performed under suitable sterility conditions for an in vivo administration of the compounds obtained.

The doses of recombinant adenovirus used for infecting the cells may be adapted in accordance with different parameters, and in particular in accordance with the cell type, the pathology in question, the gene to be expressed or alternatively the treatment period desired. Generally speaking, the recombinant adenoviruses according to the invention are used for infection at doses of between $10^4$ and $10^{14}$ pfu/ml, and preferably $10^6$ to $10^{10}$ pfu/ml. The term pfu (plaque forming unit) corresponds to the infectious power of a solution of virus, and is determined by infecting a suitable cell culture (for example line 293) and measuring, generally after 2 to 4 days, the number of plaques of infected cells. The techniques of determination of the pfu titre of a viral solution are well documented in the literature.

The recombinant adenoviruses used in the context of the present invention are preferably defective, that is to say incapable of replicating autonomously in the infected cell. Generally, the genome of the defective adenoviruses used in the context of the present invention hence lacks at least the sequences needed for replication of the said virus in the infected cell. These regions may be either removed (wholly or partially), or rendered nonfunctional, or replaced by other sequences, and in particular by the heterologous DNA sequence. Preferably, the defective virus nevertheless retains the sequences of its genome which are needed for encapsidation of the viral particles.

There are different serotypes of adenovirus, the structure and properties of which vary somewhat. Nonetheless, these viruses are not pathogenic in man, and, in particular, non-immunosuppressed subjects. Among these serotypes, it is preferable to use, in the context of the present invention, human adenoviruses type 2 or 5 (Ad 2 or Ad 5) or adenoviruses of animal origin (see Application FR 93/05,954). Among adenoviruses of animal origin which are usable in the context of the present invention, there may be mentioned adenoviruses of canine, bovine, murine [for example Mav1, Beard et al., Virology 75 (1990) 81], ovine, porcine, avian or alternatively simian (for example SAV) origin. Preferably, the adenovirus of animal origin is a canine adenovirus, and more preferably a CAV2 adenovirus [Manhattan or A26/61 (ATCC VR-800) strain, for example].

Preferably, adenoviruses of human or canine origin or of mixed origin, that is to say comprising regions originating from a human adenovirus and regions originating from a canine adenovirus, are used in the context of the invention.

The defective recombinant adenoviruses according to the invention may be prepared by any technique known to a person skilled in the art [Levero et al., Gene 101 (1991) 195, EP 185 573; Graham, EMBO J. 3 (1984) 2917]. In particular, they may be prepared by homologous recombination between an adenovirus and a plasmid carrying, inter alia, the heterologous DNA sequence. Homologous recombination takes place after cotransfection of the said adenovirus and said plasmid into a suitable cell line. The cell line used should preferably (i) be transformable by the said elements, and (ii) contain the sequences capable of complementing the portion of the defective adenovirus genome, preferably in integrated form in order to avoid risk of recombination. As an example of a line, the human embryonic kidney line 293 [Graham et al., J. Gen. Virol. 36 (1977) 59], which contains, in particular, integrated in its genome, the left-hand portion of the genome of an AdS adenovirus (12%), may be mentioned. Strategies of construction of vectors derived from adenoviruses have also been described in Applications Nos. FR 93/05,954 and FR 93/08,596, which are incorporated in the present application by reference.

Thereafter, the adenoviruses which have multiplied are recovered and purified according to standard molecular biology techniques, as illustrated in the examples.

As stated above, the recombinant adenoviruses used in the context of the present invention comprise a heterologous DNA sequence coding for a therapeutic product. The therapeutic product can be any RNA, peptide, polypeptide or protein whose production in the body is desired.

Preferably, the heterologous DNA sequence also comprises expression signals enabling the therapeutic product to be produced in the infected cells. These can be sequences which are naturally responsible for the expression of this therapeutic product when these sequences are capable of functioning in the infected cell. They can also be sequences of different origin (responsible for the expression of other proteins, or even synthetic sequences). In particular, they can be promoter sequences of eukaryotic or viral genes. For example, they can be promoter sequences originating from the genome of the cell which it is desired to infect. Similarly, they can be promoter sequences originating from the genome of a virus, including the adenovirus used. In this connection, the E1A, MLP, CMV, RSV, PGK, and the like, promoters may, for example, be mentioned. In addition, these expression sequences may be modified by the addition of activating, regulatory, and the like, sequences. Moreover, when the inserted gene does not contain expression sequences, it may be inserted in the genome of the defective virus downstream of such a sequence.

More preferably, the heterologous DNA sequence comprises signals enabling the therapeutic product to be produced and secreted by the implanted infected cells. In effect, the neovascularization of the implants according to the invention permits an especially effective release of the therapeutic products into the circulation, the release being, furthermore, sustained and controlled. To this end, the heterologous DNA sequence generally contains, upstream of the therapeutic gene, a signal sequence directing the synthesized therapeutic product into the pathways of secretion of the infected cell. This signal sequence can be the natural signal sequence of the therapeutic product, but it can also be any other signal sequence which is functional in the infected cell, or an artificial signal sequence.

Advantageously, the therapeutic product is chosen from enzymes (such as, in particular, superoxide dismutase, catalase, amylases, lipases, amidases, chymosin, and the like), blood derivatives (such as serum albumin, alpha- or beta-globin, factor VII, factor VIII, factor IX, von Willebrand factor, fibronectin, alpha$_1$-antitrypsin, and the like), insulin and its variants, lymphokines (such as interleukins, interferons, colony stimulating factors [G-CSF, GM-CSF, M-CSF, SCF, etc.], TNF, TRF, and the like), growth factors (such as growth hormone, erythropoietin, parathyroid hormone, FGF, EGF, PDGF, TGF, BDNF, NGF, CNTF, and the like), apolipoproteins or alternatively antigenic polypeptides for the production of vaccines (hepatitis, cytomegalovirus, Epstein-Barr, herpes, and the like).

As stated above, the implants according to the invention are especially advantageous in the sense that they make it possible to control the release of the therapeutic product into the body: this release is determined, in the first place, by the multiplicity of infection and by the number of cells implanted. Thereafter, the release may be controlled either by removing the implant, which permanently stops the treatment, or by the use of regulable expression systems enabling the expression of the therapeutic genes to be induced or repressed.

For the preparation of the compositions according to the invention, different types of gelling agents may be employed. The gelling agents are used to promote anchorage of the cells to the support by inclusion of the cells in a matrix having the constitution of a gel. Different cell adhesion agents may hence be used, such as, in particular, collagen, gelatin, glycosaminoglycans, fibronectin, lectins, and the like. Preferably, collagen is used in the context of the present invention. It can be collagen of human, bovine or murine origin. More preferably, type I or III collagen is used.

As stated above, the compositions according to the invention also comprise a support permitting anchorage of the cells. The term anchorage denotes any form of biological and/or chemical and/or physical interaction giving rise to adhesion and/or attachment of the cells to the support. Moreover, the cells can either coat the support used or enter within this support, or both. It is preferable, in the context of the invention, to use a solid, non-toxic and/or biocompatible support. In particular, polytetrafluoro-ethylene (PTFE) fibres may be used. In a particular embodiment of the invention, a support of biological origin such as, in particular, crosslinked collagen, bone powder, carbohydrate-based polymers and limestone-based supports.

The subject of the present invention is also a process for preparing a composition as defined above, according to which the following steps are performed:

a) a tissue sample is removed from a body,
b) the desired cells (fibroblasts, endothelial, epithelial or glial cells, hepatocytes, keratinocytes, myoblasts, and the like) are isolated and cultured in vitro,
c) the cells obtained in b) are infected with a recombinant adenovirus comprising a heterologous DNA sequence coding for a therapeutic product,
d) the infected cells are incubated with a medium containing a gelling agent,
e) the mixture obtained in d) is deposited on a support, where appropriate after coating of the latter with the gelling agent,
f) the mixture obtained in e) is incubated under conditions permitting gelation of the gelling agent and anchorage of the cells to the support, and
g) the composition obtained, which constitutes the implant which is usable for implantation, is recovered.

As stated above, steps a) and b) of the process can be avoided if the starting material comprises secondary cultures or cells extracted from cell banks. More preferably, before step d), the infected cells are washed several times. Thereafter, for the preparation of the implant, the infected cells are cultured in the presence of the gelling agent and then, when the matrix is formed, it is deposited on the support, where appropriate after bringing the latter into contact with the gelling agent. Furthermore, the cells or the support may also be brought into contact with growth factors, such as angiogenic factors, promoting the formation of the implant. In this case, traces of growth factor may persist in the implant. The support/gelling agent/cells mixture is thereafter incubated for a sufficient period to permit gelation of the gelling agent, and the matrix thereby obtained is then maintained in culture medium in order to enable the cells to anchor themselves to the support. The implant thus prepared may be implanted directly in the body.

Methods of preparation of implants have also been described by Moullier et al. [Nature Genetics 4 (1993) 154], which methods may be adapted by a person skilled in the art to the implants according to the invention (see also FR 93/09,185 and FR 93/04,700).

The invention also relates to a method for the treatment of disorders, comprising the implantation of a composition as is defined above, capable of producing a therapeutic product which is able to correct the said disorder. Preferably, this method is applicable to treatment of disorders resulting from a deficiency of a therapeutic product, and the implant is capable of producing the said product. Still more preferably the method according to the invention is usable for the treatment of thalassaemia and of deficiencies of erythropoietin (renal insufficiency, and the like), growth hormone, apolipoproteins, thyroid hormone, coagulation factors, and the like. Advantageously, the method according to the invention comprises implantation in the peritoneal cavity, in the subcutaneous tissue (suprapubic region, iliac or inguinal fossae, and the like), in an organ, a muscle, a tumour or the central nervous system, or alternatively under a mucosa.

The present invention will be described more completely by means of the examples which follow, which are to be regarded as illustrative and non-limiting.

EXAMPLES

Figure 1:
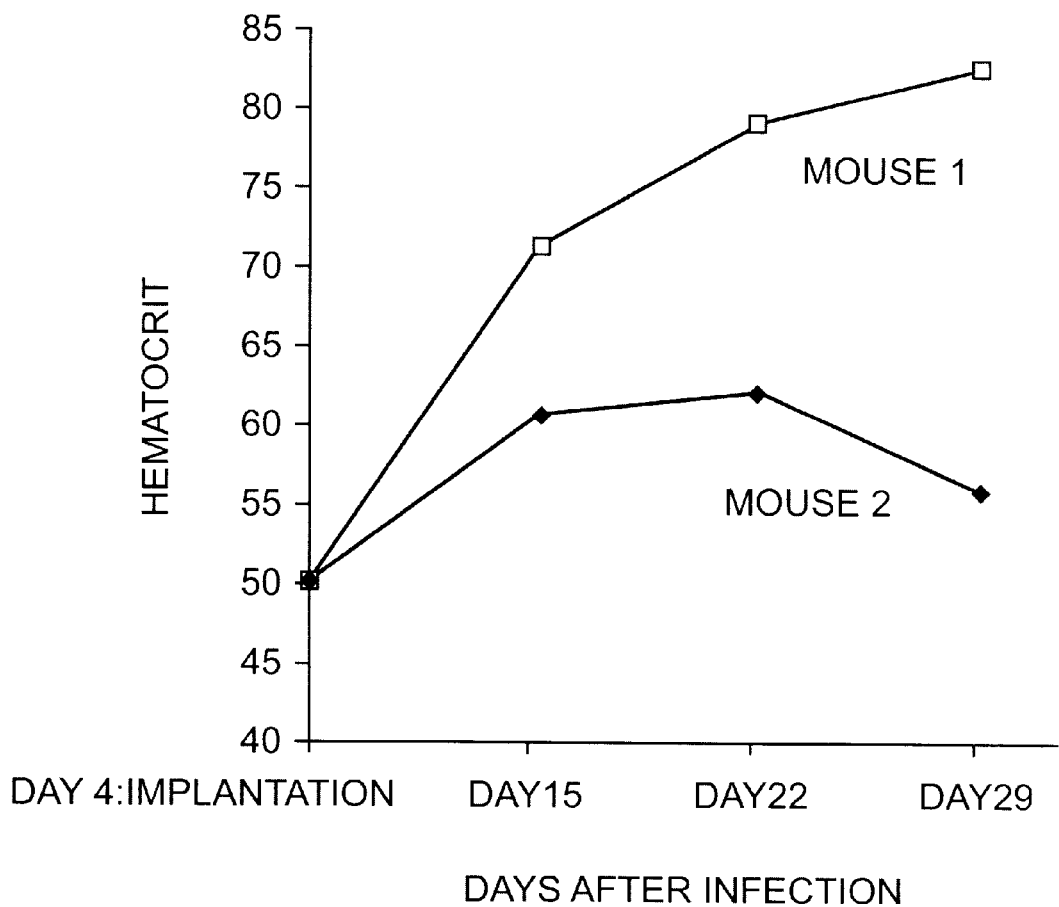
FIG. 1: Implants that secrete monkey EPO increase the hematocrit in mice.

1. General Techniques 1.1. Isolation and Culture of Fibroblasts

Fibroblasts were obtained from cutaneous biopsies carried out under sterile conditions. To this end, one or more skin fragments are removed, shredded and subjected to an enzymatic digestion. For this purpose, the shredded fragments are incubated at 37° C. with gentle agitation in a DMEM medium supplemented with 2 mM L-glutamine, streptomycin and foetal calf serum (250 μg/ml). After 2 hours, the solution is centrifuged at 1500 rpm and the cell pellet is washed twice in the same medium without enzymes. The cells are then counted and inoculated, on the basis of $4 \times 10^6$ living cells/flask, into flasks containing approximately 25 ml of the same medium.

1.2. Infection of Fibroblasts with a Recombinant Adenovirus

The infection of fibroblasts with a recombinant adenovirus is advantageously performed with a purified solution of adenovirus, for example purified on caesium chloride (see Example 2.2.). The value of such a protocol lies, in particular, in the fact that, contrary to retroviruses, a single cycle of infection suffices for obtaining a very high percentage of infected cells (up to 100%). Furthermore, the value of adenoviruses also lies in the fact that very high multiplicities of infection may be employed (1000 pfu per cell, for example).

In general, cells at confluence are incubated in the presence of a concentrated solution containing a particular amount of recombinant adenovirus. The multiplicity of infection may be adapted as appropriate by a person skilled in the art. After approximately one hour, culture supernatant is added and the cells are maintained overnight. The cells are then washed in a medium without virus, harvested and washed again. The cells are then incorporated in the medium containing the gelling agent. The percentage of infection is then checked. Although it is not generally necessary, it is then possible to perform further cycles of infection in order to increase the number of copies per cell. Moreover, this protocol may be applied to other cell types such as endothelial, epithelial or glial cells, hepatocytes, keratinocytes or myoblasts.

1.3. Preparation of Implants

The support used (synthetic or biological support) is sterilized, preferably by autoclaving, and then coated with type I collagen. More especially, in the case of polytetrafluoroethylene fibres (Gore and Associates), the addition of collagen is performed by dipping the fibres for approximately 1 hour into a solution containing collagen [0.1 N acetic acid solution containing 0.1% of rat collagen (Sigma)]. Preferably, this operation is carried out under vacuum in order to drive out the air present in the fibres. The support thereby obtained, coated with a film of collagen, is transferred to Petri dishes and dried. A solution comprising growth factors diluted in phosphate buffer is then added (10–20 ng of basic FGF per 50 mg of fibres). The support is then placed in wells or dishes whose size corresponds to that of the desired implants. The cells infected with recombinant adenoviruses are suspended in RPMI medium comprising collagen and basic FGF. This cell suspension is then deposited on the support. After gelation of the collagen (approximately 30 minutes at 37° C. under 5% $CO_2$), the gel lattices are detached from the wells using a needle, and then maintained at room temperature for 48 to 96 hours depending on the speed of retraction (the medium is changed after 48 hours). The composition obtained is ready for implantation.

1.4. Implantation

The compositions described above are implanted under anaesthesia in the intraperitoneal regions having the best vascularization, for example in the omentum majus. One or more implants may be introduced into the same body at the same site or at different sites (up to 10, for example, depending on the therapeutic gene, the pathology, the size of the implant, and the like). After implantation, it is possible to produce a pocket so as to maintain the implant or implants and to facilitate their excision. In general, vascular connections become established from the first few days, permitting an effective release of the therapeutic product.

It is also possible to implant the compositions of the invention in the subcutaneous tissue (suprapubic region, iliac or inguinal fossae, and the like), in an organ or a muscle or alternatively under a mucosa.

2. Construction of a Recombinant Adenovirus Comprising a Heterologous DNA Sequence Coding for Erythropoietin Erythropoietin (Epo) is a hormone specific for the terminal proliferation and the differentiation of red cell precursors. Its gene has been cloned, sequenced and expressed in vitro (EP 148,605). Recombinant Epo is widely used to replace the deficit of production by the kidney in cases of chronic renal insufficiency. At high dose, Epo also has a potential therapeutic value for genetically determined anaemias (β-thalassaemia, depranocytosis) and some deficiencies of haematopoiesis. For all these applications, the sustained and controlled production of Epo by means of an implant according to the invention constitutes a considerable advance and enables the prohibitive costs of high doses of recombinant Epo to be reduced.

2.1. Construction of Plasmid pAd.RSV.Epo

Plasmid pAd.RSV.Epo was constructed from plasmid pAd.RSV.βGal [Stratford-Perricaudet et al., J. Clin. Invest. (1992) 626] by replacement of the β-gal gene by the Epo gene.

For this purpose, cDNA coding for monkey Epo and containing its own secretion signal was isolated from the Bluescript plasmid in the form of an XhoI-EcoRV fragment. This fragment was then cloned at the SalI site (located after the RSV LTR) and EcoRV site (located before the AdS PIX) of the vector pAd.RSV.βGal, resulting in replacement of the β-gal gene by the Epo cDNA.

2.2. Construction of the Defective Recombinant Adenovirus Ad.RSV.Epo

The adenovirus Ad.RSV.Epo was obtained by homologous recombination in vivo between the mutant adenovirus Ad.dl1324 [Thimmappaya et al., Cell 31 (1982) 543] and the vector pAd.RSV.Epo.

For this purpose, plasmid pAd.RSV.Epo and the adenovirus Ad.dl1324 linearized with the enzyme ClaI were cotransfected into line 293 in the presence of calcium phosphate, to permit homologous recombination. The recombinant adenoviruses thus generated were selected by plaque purification. After isolation, the DNA of the recombinant adenovirus was amplified in cell line 293, leading to a culture supernatant containing the unpurified defective recombinant adenovirus having a titre of approximately $10^{10}$ pfu/ml.

The viral particles are generally purified by centrifugation on a caesium chloride gradient according to known techniques (see, in particular, Graham et al., Virology 52 (1973) 456). The adenovirus Ad.RSV.Epo may be stored at −80°C. in 20% glycerol.

3. Preparation of an Implant Comprising Fibroblasts Infected with the Recombinant Adenovirus Ad.RSV.Epo, Collagen and Polytetrafluoroethylene (PTFE) Fibres Fibroblasts ($10^7$ cell/ml), prepared from the skin of DBA2J mice according to the protocol described in Example 1.1, were infected at confluence with the adenovirus Ad.RSV.Epo purified on a caesium chloride gradient as described in Example 2 (1 single cycle of infection). Two infection conditions were used, corresponding to two titres, namely $10^8$ and $10^9$ pfu, equivalent to a multiplicity of infection of 10 and 100, respectively.

24 hours after infection, the cells were washed, trypsinized and then harvested. After a further wash, 4 implants were prepared according to the protocol described in Example 1.3., comprising $10^7$ cells each (2 implants for each viral titre).

The implants obtained after 72 hours of culture were removed and then implanted in the peritoneum of two 8-week-old DBA2J mice according to the protocol described in Example 1.4. (2 implants per mouse). Mouse 1 contains the 2 implants prepared with fibroblasts infected with a viral tire of $10^9$ pfu. Mouse 2 contains the 2 implants prepared with fibroblasts infected with a viral titre of $10^8$ pfu.

The expression of Epo in vivo was assayed in the blood, and its effect was determined by measuring the rise in haematocrit, which reflects the physiological action of Epo, that is to say the increase in the number of red cells. For this purpose, blood samples are withdrawn by puncture at the retroorbital sinus by means of a microhaematocrit tube, and then centrifuged in a microhaematocrit centrifuge. The results obtained are presented in FIG. 1. They show clearly that the implants according to the invention induce a substantial and dose-dependent increase in the haematocrit.

What is claimed is:

1. A composition for transplantation in vivo comprising proliferating cells, a gelling agent, and a support to which said cell are anchored, wherein said cells comprise a replication defective recombinant adenovirus comprising at least one functional adenoviral gene and a heterologous DNA sequence coding for a therapeutic product, whereby the heterologous DNA sequence is expressed and the product is produced.

2. The composition according to claim 1, wherein said cells are selected from the group consisting of fibroblasts, endothelial cells, epithelial cells, glial cells, hepatocytes, keratinocytes and myoblasts.

3. The composition according to claim 2, wherein said cells are fibroblasts.

4. The composition according to claim 1, wherein the cells are autologous with respect to an intended patient.

5. The composition according to claim 1, wherein the adenovirus is an adenovirus of human origin, canine origin, or an adenovirus comprising regions originating from a human adenovirus and a canine adenovirus.

6. The composition according to claim 5, wherein the adenovirus is selected from the group consisting of Ad2, Ad5 and CAV2.

7. The composition according to claim 1, wherein the therapeutic product is selected from the group consisting of peptides, polypeptides and proteins.

8. The composition according to claim 7, wherein the heterologous DNA sequence comprises signals enabling the therapeutic product to be produced and secreted.

9. The composition according to claim 7, wherein the therapeutic product is selected from the group consisting of enzymes, blood derivatives, insulin, variants of insulin, lymphokines, growth factors, apolipoproteins and antigenic polypeptides for the production of vaccines.

10. The composition according to claim 9, wherein said enzymes are selected from the group consisting of superoxide dismutase, catalase, amylases, lipases, amidases, and chymosin.

11. The composition according to claim 9, wherein said blood derivatives are selected from the group consisting of serum albumin, alpha-globin, beta-globin, factor VII, factor VIII, factor IX, von Willebrand factor, fibronectin and alpha$_1$-antitrypsin.

12. The composition according to claim 9, wherein said lymphokines are selected from the group consisting of the interleukins, interferons, colony stimulating factors, TNF, and TRF.

13. The composition according to claim 12, wherein said colony stimulating factors are selected from the group consisting of G-CSF, GM-CSF, M-CSF, and SCF.

14. The composition according to claim 9, wherein said growth factors are selected from the group consisting of growth hormone, erythropoietin, parathyroid hormone, FGF, EGF, PDGF, TGF, BNDF, NGF, and CNTF.

15. The composition according to claim 9, wherein said antigenic polypeptides are selected from the group consisting of antigens from hepatitis virus, cytomegalovirus, Epstein-Barr virus, and herpes virus.

16. The composition according to claim 1, wherein the gelling agent is selected from the group consisting of collagen, gelatin, glycosaminoglycans, fibronectin and lectins.

17. The composition according to claim 1, wherein the support is a solid, non-toxic and biocompatible support.

18. The composition according to claim 17, wherein the support is a biological support.

19. The composition according to claim 17, wherein the support is selected from the group consisting of crosslinked collagen, bone powder, carbohydrate-based polymers and limestone-based supports.

20. The composition according to claim 17, wherein the support is selected from polytetrafluoroethylene fibres.

21. A process for preparing the composition according to claim 1 comprising:
   a) removing a tissue sample from a body,
   b) isolating and culturing desired cells from said tissue sample,
   c) infecting the cultured cells with a replication defective recombinant adenovirus comprising at least one functional adenoviral gene and a heterologous DNA sequence coding for a therapeutic product, whereby the heterologous DNA sequence is expressed and the product is produced,
   d) incubating the infected cells with a medium containing a gelling agent thereby forming a mixture,
   e) depositing the mixture on a support,
   f) incubating the mixture under conditions permitting gelation of the gelling agent and anchorage of the cells to the support, and
   g) recovering the composition obtained in step (f).

22. The process according to claim 21, wherein the support in step e) is coated with the gelling agent.

23. The composition according to claim 1, comprising between $10^5$ and $10^{10}$ cells.

24. The composition according to claim 1, comprising between $10^5$ and $10^8$ cells.

25. The composition according to claim 1, wherein the heterologous DNA sequence comprises a signal sequence.

* * * * *